(12) United States Patent
Li et al.

(10) Patent No.: US 10,139,355 B1
(45) Date of Patent: Nov. 27, 2018

(54) METHOD FOR HIGH PRECISION IMAGING FOR THREE-DIMENSIONAL TOPOGRAPHY OF CRACKS IN HYDRAULIC FRACTURING TEST OF ROCKS

(71) Applicant: Institute of Geology and Geophysics, Chinese Academy of Sciences, Beijing (CN)

(72) Inventors: Shouding Li, Beijing (CN); Linan Liu, Beijing (CN); Xiao Li, Beijing (CN); Zhongming Zhou, Beijing (CN); Zhenxing Zhang, Beijing (CN); Yanhui Liu, Beijing (CN)

(73) Assignee: Institute of Geology and Geophysics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 16/025,065

(22) Filed: Jul. 2, 2018

(30) Foreign Application Priority Data

Jul. 31, 2017 (CN) .......................... 2017 1 0635873

(51) Int. Cl.
*G01N 3/46* (2006.01)
*G01N 23/046* (2018.01)
*G01N 1/28* (2006.01)

(52) U.S. Cl.
CPC ............ *G01N 23/046* (2013.01); *G01N 1/28* (2013.01); *G01N 2223/309* (2013.01); *G01N 2223/616* (2013.01); *G01N 2223/646* (2013.01)

(58) Field of Classification Search
None
See application file for complete search history.

(56) References Cited

U.S. PATENT DOCUMENTS

| 5,297,420 A * | 3/1994 | Gilliland | G01N 15/08 73/38 |
| 8,081,796 B2 * | 12/2011 | Derzhi | E21B 49/005 378/53 |
| 2018/0106708 A1 * | 4/2018 | Siebrits | G01N 23/046 |

* cited by examiner

*Primary Examiner* — Hoon K Song
(74) *Attorney, Agent, or Firm* — Maier & Maier, PLLC

(57) ABSTRACT

A method for imaging three-dimensional topography with high precision, which overcomes the disadvantage and deficiency of low precision in observing three-dimensional topography of hydraulically fractured cracks of rocks, improve the precision in observing three-dimensional topography of cracks in rock hydraulic fracturing test, and benefit for scientifically understanding regular pattern of development of hydraulically fractured cracks of rocks. The technical solution comprises: hydraulically fracturing the rock with aqueous solution containing fluorine nuclides; forming hydraulically fractured cracks; in the process of fracturing, loading a fracturing apparatus while rotating the same; emitting an x-ray beam from an x-ray source, which penetrates the rock and reaches a CT detector; optical signals transmitted by the fluorine nuclides inside the rock being received by a high resolution planar array SiPM detector for nuclides; performing image fusion of nuclides tomographic scanning data and CT data to implement high precision imaging for three-dimensional topography of cracks in rocks.

7 Claims, 1 Drawing Sheet

METHOD FOR HIGH PRECISION IMAGING FOR THREE-DIMENSIONAL TOPOGRAPHY OF CRACKS IN HYDRAULIC FRACTURING TEST OF ROCKS

TECHNICAL FIELD

The present application relates to technology field of rock mechanics tests.

BACKGROUND

Three-dimensional topography distribution of cracks is one of the important measurements of physical quantities in a hydraulic fracturing test of rocks. Presently, an observation of the surface cracks in hydraulic fracturing test of rocks mainly depends on the means of scanning electron microscopes, etc., while an observation of the internal three-dimensional topography mainly depends on the x-ray CT imaging technology. The x-ray CT imaging technology has a higher positioning precision, but a limited imaging precision, for cracks in hydraulic fracturing test of rocks. Presently, industrial CT is incapable of imaging cracks with widths less than 0.1 mm in a rock sample which has a diameter of 100 mm, whereas about 86% of cracks have a width less than 0.1 mm in a hydraulic fracturing test, hence, industrial CT is incapable of effectively observing a majority of cracks in a hydraulic fracturing test of a rock with a diameter of 100 mm, losing information of a number of existent cracks.

Therefore, current methods for observing cracks in a hydraulic fracturing test of rocks fail to satisfy the needs of observing three-dimensional topography of cracks in a hydraulic fracturing test of rocks.

SUMMARY

The present application provides a method for imaging three-dimensional topography with high precision, which is able to overcome the disadvantage and deficiency of low precision in observing three-dimensional topography of hydraulically fractured cracks of rocks, improve the precision in observing three-dimensional topography of cracks in a rock hydraulic fracturing test, and benefit for scientifically understanding the regular pattern of development of hydraulically fractured cracks of rocks. The technical solution comprises: hydraulically fracturing the rock with aqueous solutions containing fluorine nuclides; forming hydraulically fractured cracks; in the process of fracturing, loading a fracturing apparatus while rotating the rock, emitting an x-ray beam from an x-ray source, which penetrates the rock and reaches the CT detector; optical signals transmitted by the fluorine nuclides inside the rock being received by a high resolution planar array SiPM detector for nuclides, γ photons having strong penetration capacity and an auto-collimation feature, and image of microcracks in the rock, into which positron nuclides tracers are introduced, is a heat source image in the context of a heat sink, benefiting for acquiring high contrast image of microcracks, making up for deficiencies of CT imaging technology in microcracks imaging. Image fusion of nuclides tomographic scanning data and CT data, realizes high precision imaging for three-dimensional topography of cracks in rocks.

The primary technical solution of the method for high precision imaging for three-dimensional topography of cracks in rock hydraulic fracturing test consists of three parts: a high precision rotary hydraulic fracturing testing machine for rocks, a laboratory x-ray industrial CT and a high resolution planer array SiPM detector for nuclides. The high precision rotary hydraulic fracturing testing machine for rocks is characterized by consisting of a rock sample 1, an upper spacer 2, a lower spacer 3, a high precision rotary actuator 4, a rotary mechanism 5, a peripheral pressurizing pump 6, a self-balancing piston 7, an axial actuator 8, a triaxial cylinder 9, a counter force frame 11 and a high pressure water pump 12 containing fluorine nuclides solution, etc., wherein the rock sample 1 is disposed between the upper spacer 2 and the lower spacer 3, the triaxial cylinder 9 and the peripheral pressurizing pump 6 implement peripheral pressure loading for the rock sample 1, the self-balancing piston 7 and the axial actuator 8 ensure implementation of axial loading for the rock sample 1, the fluorine nuclides solution fractures the rock sample 1 to form fractured cracks 10 in the rock sample 1 via the high pressure water pump 12 containing fluorine nuclides solution, when the hydraulic fracturing testing machine for rocks is loaded for peripheral pressure, axial compression and hydraulic fracturing, the high precision rotary actuator 4 and the rotary mechanism 5 drive the rock sample 1 to rotate at a certain rate; the laboratory x-ray industrial CT is characterized by consisting of apparatuses such as an x-ray source 13, a CT detector 15, etc. An x-ray beam 14 is emitted from the x-ray source 13 penetrating the rock sample 1 and being received by the CT detector 15 after penetration, then a CT image being calculated based on a distribution $\mu(x,y)$ of linear attenuation coefficient; the high resolution planar array SiPM detector for nuclides is characterized by consisting of apparatuses including the high pressure water pump 12 containing fluorine nuclides solution and a high resolution planar array SiPM detector for nuclides 16, etc. The fluorine nuclides solution is pressed into the rock sample 1 by the high pressure water pump 12 containing a fluorine nuclides solution, and fractures the rock sample 1 to form the fractured cracks 10 in the rock sample 1, the fluorine nuclides in the cracks annihilate and emit optical signals, which are received by the high resolution planar array SiPM detector for nuclides 16, and then converted into electrical signals for imaging.

Fundamental Principle and Technology

A CT image of x-rays penetrating a rock reflects an absorption level for x-rays in various positions of the rock, where a mineral density in the rock is proportional to an x-ray absorption coefficient, the larger a difference between adjacent mineral densities is, the greater a contrast of CT images of x-rays is, and the higher a resolution is. The positron fluorine nuclides are radioactive nuclides, wherein a positron annihilates and produces a pair of γ proton, the protons hit the SiPM detector for nuclides and are located, the received optical signals are converted into electrical signals via the high resolution planar array SiPM detector for nuclides to implement data reassembling and image reconstruction. Two SiPM planar detectors are disposed face to face, where a sample to be tested is rotating with high precision, to implement complete data acquisition. The CT imaging of x-ray has an advantage of high precision in imaging a structure of a rock, and the fluorine nuclides tomographic microimaging has an advantage of high sensitivity in imaging locations, thus performing image fusion of the CT image of x-ray and the nuclides tomographic microimage, to provide a method for high precision imaging for three-dimensional topography of cracks in hydraulic fracturing test of rocks. The method comprises: pressing the fluorine nuclides solutions into the rock sample with the high pressure water pump containing fluorine nuclides solutions; fracturing the rock sample to form cracks in the rock sample; in the process of hydraulic fracturing of rocks, the hydraulic fracturing testing machine for rocks rotating with high precision at a certain rate, and in the process of hydraulic fracturing of rocks, an x-ray beam emitted from an x-ray source penetrating the rock and being received by the CT detector to be used for imaging; performing high precision imaging for the structure of the rock; at the same time, optical signals transmitted by the fluorine nuclides inside the cracks of the rock performing high precision imaging for the locations of cracks, after being received by a high resolution planar array SiPM detector for nuclides and converted into electrical signals; finally performing image fusion of the CT image and the nuclides tomographic microimage, to implement high precision imaging for three-dimensional topography of cracks in rocks.

The primary technical solution of the method for high precision imaging for three-dimensional topography of cracks in rock hydraulic fracturing test comprises three parts: a high precision rotary hydraulic fracturing testing machine for rocks, a laboratorial x-ray industrial CT and a high resolution planer array SiPM detector for nuclides.

The high precision rotary hydraulic fracturing testing machine for rocks is characterized by consisting of a rock sample 1, an upper spacer 2, a lower spacer 3, a high precision rotary actuator 4, a rotary mechanism 5, a peripheral pressurizing pump 6, a self-balancing piston 7, an axial actuator 8, a triaxial cylinder 9, a counter force frame 11, and a high pressure water pump 12 containing fluorine nuclides solution, etc., wherein the rock sample 1 is disposed between the upper spacer 2 and the lower spacer 3, the triaxial cylinder 9 and the peripheral pressurizing pump 6 implement peripheral pressure loading for the rock sample 1, the self-balancing piston 7 and the axial actuator 8 ensure the implementation of axial loading for the rock sample 1, the fluorine nuclides solutions fracture the rock sample 1 to form fractured cracks 10 in the rock sample 1 via the high pressure water pump 12 containing fluorine nuclides solution, when the hydraulic fracturing testing machine for rocks is loaded for peripheral pressure, axial compression and hydraulic fracturing, the high precision rotary actuator 4 and the rotary mechanism 5 drive the rock sample 1 to rotate at a certain rate.

The laboratorial x-ray industrial CT is characterized by consisting of apparatuses such as an x-ray source 13, a CT detector 15, etc. An x-ray beam 14 emitted from the x-ray source 13 penetrates the rock sample 1 and is received by the CT detector 15 after penetration, then a CT image is formed based on a distribution $\mu(x,y)$ of linear attenuation coefficient.

The high resolution planar array SiPM detector for nuclides is characterized by consisting of apparatuses including the high pressure water pump 12 containing fluorine nuclides solution and a high resolution planar array SiPM detector for nuclides 16, etc. The fluorine nuclides solution is pressed into the rock sample 1 by the high pressure water pump 12 containing fluorine nuclides solution, and fractures the rock sample 1 to form the fractured cracks 10 in the rock sample 1, the fluorine nuclides in the crack(s) annihilate and emit optical signals, which are received by the high resolution planar array SiPM detector for nuclides 16, and then converted into electrical signals for imaging.

DESCRIPTION OF EMBODIMENTS

Figure 1:
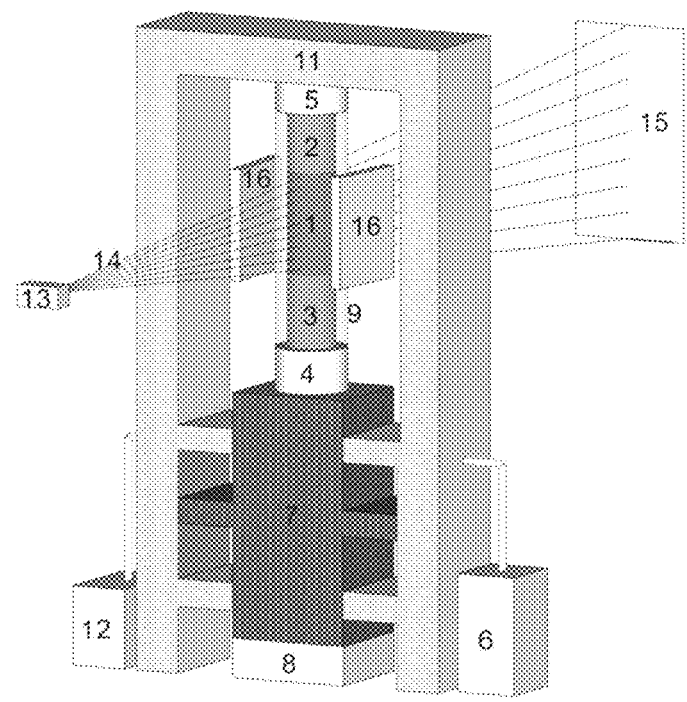
FIG. 1 shows system for high precision imaging for three dimensional topography of cracks in a rock hydraulic fracturing test.
Figure 2:
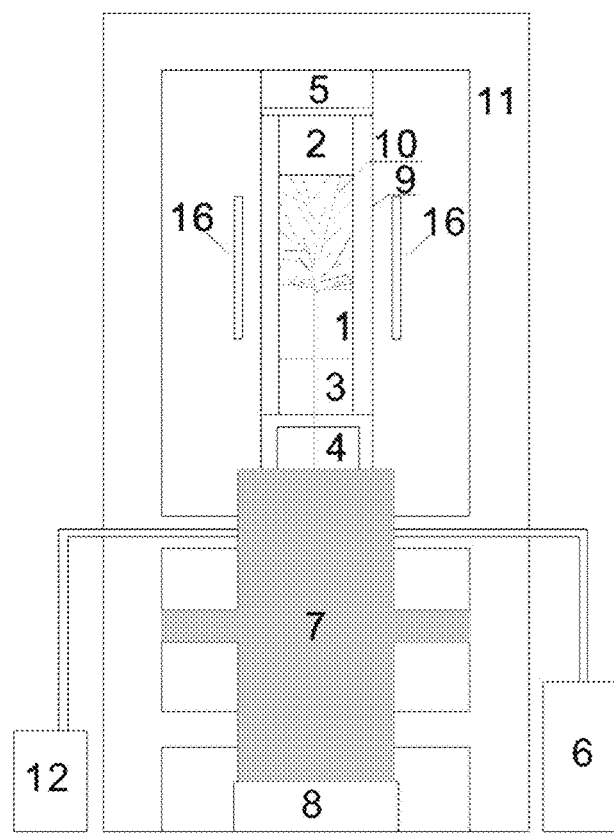
FIG. 2 shows a system for high precision imaging for three dimension topography of cracks in a rock hydraulic fracturing test, where
1: rock sample;
2: upper spacer;
3: lower spacer;
4: high precision rotary actuator;
5: rotary mechanism;
6: peripheral pressurizing pump;
7: self-balancing piston;
8: axial actuator,
9: triaxial cylinder;
10: fractured crack;
11: counter force frame;
12: high pressure water pump;
13: x-ray source;
14: x-ray beam;
15: CT detector;
16: high resolution planar array SiPM detector for nuclides.

1. First, formulating a fluorine nuclides solution with highly concentrated fluorine nuclides, and adding the fluorine nuclides solution into the high pressure water pump 12.
2. Disposing the rock sample 1 between the upper spacer 2 and the lower spacer 3, the triaxial cylinder 9 and the peripheral pressurizing pump 6 implementing peripheral pressure loading for the rock sample 1, the self-balancing piston 7 and the axial actuator 8 ensuring implementation of axial loading for the rock sample 1, the fluorine nuclides solution fracturing the rock sample 1 to form fractured cracks 10 in the rock sample 1 via the high pressure water pump 12 containing fluorine nuclides solution, when the hydraulic fracturing testing machine for rocks is loaded for peripheral pressure, axial compression and hydraulic fracturing, the high precision rotary actuator 4 and the rotary mechanism 5 driving the rock sample 1 to rotate at a certain rate.
3. Running the laboratorial x-ray industrial CT, an x-ray beam 14 emitted from the x-ray source 13 penetrating the rock sample 1, and being received by the CT detector 15 after penetration, then CT images being calculated based on a distribution $\mu(x,y)$ of linear attenuation coefficient, precisely locating the locations of cracks distribution.
4. Pressing the fluorine nuclides solution into the rock sample 1 with the high pressure water pump 12 containing fluorine nuclides solution, fracturing the rock sample 1 to form fractured cracks 10 in the rock sample 1, which are filled with fluorine nuclides solution, the fluorine nuclides in the cracks annihilating and emitting optical signals, which are converted into electrical signals to proceed with imaging after being received by the high resolution planar array SiPM detector for nuclides 16, imaging the microcracks which are unable to be observed with CT images.
5. Performing image fusion of the CT images and the nuclides tomographic microimages, to implement high precision imaging for three-dimensional topography of hydraulically fractured cracks in rocks.

What is claimed is:
1. A system for high precision imaging for three-dimensional topography of cracks in a rock hydraulic fracturing test, comprising: a high precision rotary hydraulic fracturing testing machine for rocks and a laboratorial x-ray industrial CT, wherein said high precision rotary hydraulic fracturing testing machine for rocks includes a frame, a support device, a rotation device, a peripheral pressurizing device and an axial pressurizing device at least partially disposed within the frame as well as a high pressure water pump at least partially disposed outside the frame, wherein the support device is used for clamping a rock sample from upper and lower sides of the rock sample, the rotation device is connected with the support device and used for rotating the rock sample, the peripheral pressurizing device is disposed to surround the rock sample and used for applying pressure on periphery of the rock sample, the axial pressurizing device is provided below the rotation device and used for applying axial pressure to the rock sample, the high pressure water pump is used for supplying fracturing fluid into the rock sample to form fractured cracks within the rock sample, wherein the laboratorial x-ray industrial CT is used for forming a CT image of the fractured cracks in the rock sample, wherein the fracturing fluid is solution containing fluorine nuclides, and the system further comprises a high resolution planar array SiPM detector for nuclides which is used for receiving optical signals emitted by fluorine nuclides in the fractured cracks and then converting the optical signals into electrical signals for imaging.

2. The system as defined by claim 1, wherein the rotation device includes a high precision rotary actuator disposed above the axial pressurizing device and a rotary mechanism connected to the frame, and the high precision rotary actuator and the rotary mechanism cooperate to rotate the rock sample.

3. The system as defined by claim 2, wherein the support device includes an upper spacer connected to the rotary mechanism and a lower spacer connected to the high precision rotary actuator, and the upper spacer and the lower spacer support the rock sample from upper and lower sides of the rock sample respectively.

4. The system as defined by claim 3, wherein the peripheral pressurizing device includes a triaxial cylinder and a peripheral pressurizing pump in communication with the triaxial cylinder, and the peripheral pressurizing pump supplies power for the triaxial cylinder to apply peripheral pressure to the rock sample.

5. The system as defined by claim 4, wherein the axial pressurizing device includes a self-balancing piston disposed below the high precision rotary actuator and an axial actuator disposed below the self-balancing piston, and the axial actuator applies axial pressure to the rock sample through the self-balancing piston.

6. The system as defined by claim 5, wherein the laboratorial x-ray industrial CT includes an x-ray source and a CT detector, the x-ray source is used for emitting x-ray beam, the CT detector is used for receiving the x-ray beam penetrating the rock sample and forming a CT image based on a distribution of linear attenuation coefficient of the x-ray beam.

7. A method for high precision imaging for three-dimensional topography of cracks in rock hydraulic fracturing test, realized by the system of claim 6, wherein the method comprises following steps:

Step 1, putting the rock sample between the upper spacer and the lower spacer;

Step 2, peripherally pressurizing the rock sample by means of the triaxial cylinder and the peripheral pressurizing pump;

Step 3, axially pressurizing the rock sample by means of the self-balancing piston and the axial actuator, Step 4, supplying the solution containing fluorine nuclides into the rock sample by means of the high pressure pump to form the fractured cracks;

Step 5, at the same time when Steps 2, 3 and 4 being executed, rotating the rock sample by means of the high precision rotary actuator and the rotary mechanism;

Step 6, after the fractured cracks being formed within the rock sample, penetrating the rock sample by the x-ray beam emitted from the x-ray source, and receiving the x-ray beam penetrating the rock sample and forming a CT image based on a distribution of linear attenuation coefficient of the x-ray beam by the CT detector;

Step 7, receiving optical signals emitted by the fluorine nuclides in the fractured cracks and then converting the optical signals into electrical signals to form a fluorine nuclides image by the high resolution planar array SiPM detector for nuclides; and Step 8, fusing the CT image and the fluorine nuclides image to obtain a high precision image for three-dimensional topography of cracks in rock hydraulic fracturing test.

* * * * *